United States Patent
Hallett et al.

(10) Patent No.: US 7,261,939 B2
(45) Date of Patent: Aug. 28, 2007

(54) TABLETS WITH COLOURED PATTERNS AND PREPARATION THEREOF

(75) Inventors: Martin D. Hallett, West Malling (GB); Linda A. Reeves, Chislehurst (GB); Marshall Whiteman, Ditton (GB)

(73) Assignee: Phoqus Limited, Kent (GB)

( * ) Notice: Subject to any disclaimer, the term of this patent is extended or adjusted under 35 U.S.C. 154(b) by 70 days.

(21) Appl. No.: 10/476,915

(22) PCT Filed: May 2, 2002

(86) PCT No.: PCT/GB02/02043

§ 371 (c)(1), (2), (4) Date: May 18, 2004

(87) PCT Pub. No.: WO02/087550

PCT Pub. Date: Nov. 7, 2002

(65) Prior Publication Data

US 2004/0191499 A1   Sep. 30, 2004

(30) Foreign Application Priority Data

May 2, 2001   (GB) ................................ 0110846.3

(51) Int. Cl.
*B32B 5/16*   (2006.01)

(52) U.S. Cl. ...................... 428/403; 428/404; 428/405; 428/406; 428/407; 427/212; 427/218; 427/219; 427/220

(58) Field of Classification Search ................ 428/403, 428/404, 405, 406, 407; 427/212, 218, 219, 427/220
See application file for complete search history.

(56) References Cited

U.S. PATENT DOCUMENTS 4,720,378 A * 1/1988 Forse et al. ................. 424/10.2
5,354,583 A * 10/1994 Zuhr et al. .................. 427/526

FOREIGN PATENT DOCUMENTS

EP   0501553 A1 * 2/1992

* cited by examiner

*Primary Examiner*—Leszek Kiliman
(74) *Attorney, Agent, or Firm*—McAndrews, Held & Malloy, Ltd.

(57) ABSTRACT

A tablet comprising a core which is at least partially coated with an outer layer obtained by electrostatic deposition of a powder and subsequent fusing of the deposited powder to form a film characterised in that a surface of the tablet coated with said outer layer is contoured to provide higher regions and lower regions, the outer layer having a different colour in said lower regions to the outer layer in said higher regions.

18 Claims, 2 Drawing Sheets

TABLETS WITH COLOURED PATTERNS AND PREPARATION THEREOF

This invention relates to tablets, and particularly to their identification by colour or coloured patterns. More specifically, it is concerned with a method of applying colours to a tablet surface or tablet surfaces by electrodeposition to create a visible pattern thereon.

The electrostatic application of powder material to a substrate is know. Methods have already been developed in the fields of electrophotography and electrography and examples of suitable methods are described, for example, in Electrophotography and Development Physics. Revised Second Edition, by L. B. Schein, published by Laplacian Press, Morgan Hill, Calif. The electrostatic application of powder material to a solid dosage form is known and techniques are disclosed, for example, in WO01/43727, WO92/14451, WO96/35413, WO96/35516 and PCT/GB01/00425.

The technique generally involves creating a charge differential between coloured particles and the tablet or an electrode in contact with the tablet, causing the particles to be attracted to the tablet surface. This can be accomplished by applying a positive charge to coloured particles which are then electromagnetically attracted to the surface of a tablet mounted on an electrode either earthed or negatively charged. The particles are then secured to the tablet surface by a subsequent heat or fusion treatment.

Different coloured particles can be simultaneously electrodeposited on a tablet surface to establish an intermediate colour, and by using different blends of colours a wide range of intermediates can be created. It has now been found that by creating a pattern of grooves and/or recesses in a tablet surface, a differential coloured pattern can be created as a consequence of coloured particles bearing a higher charge or larger particle size being preferentially deposited as an outer layer on the bases of such grooves and recesses.

According to one aspect of the present invention there is provided a tablet comprising a core which is at least partially coated with an outer layer obtained by electrostatic deposition of a powder and subsequent fusing of the deposited powder to form a film characterised in that a surface of the tablet coated with said outer layer is contoured to provide higher regions and lower regions, the outer layer having a different colour in said lower regions to the outer layer in said higher regions.

According to a further aspect of the present invention there is provided a method of coating a surface of a tablet to create a coloured pattern thereon, in which the tablet surface is contoured to provide higher regions and lower regions, the method comprising electrostatically depositing two differently coloured particles to the surface, particles of one colour being charged to a different level and/or having a different particle size to the particles of the other colour, whereby the higher charged particles or particles of larger particle size preferentially deposit as an outer layer on the lower regions and fusing the deposited particles to form a layer having a different colour in the lower regions than in the higher regions.

The invention provides a simple effective process by which coloured patterns may be applied to tablets. The tablets may be for any purpose e.g. confectionery, pharmaceutical. Preferred tablets are pharmaceutical unit dose forms. The colour arrangement may be in the form of a pattern, letter, numeral, word, logo or any combination thereof.

Colour separation is achieved by contouring the surface of the tablet such that there are higher regions and lower regions. This is conveniently achieved by providing grooves and/or recesses in the tablet surface by use of a suitable mould. However, tablet cores may be embossed, engraved etc. to provide a contoured surface. The larger the depth between the higher and lower regions the easier it is to achieve colour separation. Preferably, the depth between the higher and lower regions is at least 0.4 mm. There appears to be no dependency on the degree of colour separation on the area of the lower regions. For example, it is possible to provide a different coloured symbol on a tablet either by creating a recess the shape of the desired symbol or by creating ridges in the shape of the desired symbol.

Preferably the boundary between the higher and lower regions is vertical or substantially vertical since this will provide a sharp contrast between two colours. Less contrast is observed when the boundary between the higher and lower regions is in the form of a small gradient.

To achieve separation of two powders, the powders can differ in there electrostatic charge and/or their particle size. Different electrostatic charges can be achieved by employing powders with a different formula of ingredients. Particle size differences can readily be achieved during the manufacturing process e.g. by grinding, sieving etc. For ease of colour separation, the differences in electrostatic charge or particle size should be large. When separation is achieved using different particle sizes, it is desirable to use powders having narrow particle size distributions to avoid an overlap between the particle size distributions.

The powders may be mixed and simultaneously applied to the table surface by electrostatic deposition. Suitable application techniques are disclosed in the above patents. The tablets are conveniently coated using a conventional dual component delivery device adapted from the electrophotographic industry, such a coating process being disclosed in WO01/43727. An AC component of the development filed is required for colour separation. A development field in the range 1 to 7 kV and a frequency in the range 500 to 4000 Hz has been found to provide good colour separation.

While best colour separation is achieved on tablets having a planar surface with grooves or recesses, it is also effective when the surface of the tablet is significantly curved. Colour separation may be achieved when the mean surface of the tablet is spherical, with a relative curvature as small as 1 cm.

A powder material for electrostatic application to a substrate should have certain properties. For example, the electrical properties of the powder material should be such as to make the powder material suitable for electrostatic application, and other properties of the powder material should be such that the material can be secured to the substrate once electrostatic application has taken place.

WO96/35413 describes a powder material which is especially suitable for electrostatic application to a poorly-conducting (non-metal) substrate such as a pharmaceutical tablet. Because it may be difficult to find a single component capable of providing the material with all the desired properties, the powder material with all the desired properties, the powder material comprises a number of different components which together are capable of providing the material with all or at least as many as possible of the desired properties, the components being co-processed to form "composite particles". For example, the powder material may comprise composite particles including one component which is fusible to form a continuous film on the surface of the substrate, and another component which has desirable electrical properties.

A potential disadvantage of the above mentioned powder materials, however, is that they are not readily adaptable to changes in formulation. The formulation of a powder material may be changed for a number of different reasons. For example, if the material is a coloured material, there may be a change in the colourant, or if the material is an active material, for example a physiologically active material there may be a change in the type of active material, or in the concentration of that active material. Because all the components of the powder material are intimately mixed, any change in the components will alter the material's electrical properties and hence its performance in electrostatic application. Whenever there is a change in formulation, it may therefore be necessary, for optimum performance, to adjust the content of the component(s) that make the material suitable for electrostatic application, or perhaps even to use a different component.

PCT/GB01/00425 discloses a method of electrostatically applying a powder material to a substrate, wherein at least some of the particles of the material comprise a core and a shell surrounding the core, the core and the shell having different physical and/or chemical properties.

Where the particles of the powder material comprise a core and a shell surrounding the core, it is possible to place those components which are likely to be altered, for example colourant in the core, and to provide a more universal shell composition which is suitable for use with various core compositions, so that alterations may be made to the components that are in the core without substantially affecting the overall suitability of the powder material; thus, the shell ensures that the change in composition of the core does not affect the performance of the material in electrostatic application. Accordingly, alterations to one component of the powder material may be made with minimum alteration in the amounts of other components.

Generally, the powder material includes a component which is fusible, and that component may be presence in the shell or in the core or in both the shell and the core. Advantageously, the fusible component is treatable to form a continuous film coating. Examples of suitable components are as follows: polyacrylates, for example polymethacrylates; polyesters; polyurethanes; polyamides, for example nylons; polyureas; polysulphones; polyethers; polystyrene; polyvinylpyrrolidone; biodegradable polymers, for example polycaprolactones, polyanhydrides, polylactides, polyglycolides, polyhydroxybutyrates and polyhydroxyvalerates; polysaccharides, for example lactitol, sorbitol xylitol, galactitol and maltitol; sugars, for example sucrose, dextrose, fructose, xylose and galactose; hydrophobic waxes and oils, for example vegetable oils and hydrogenated vegetable oils (saturated and unsaturated fatty acids) e.g. hydrogenated castor oil, carnauba wax, and beeswax; hydrophilic waxes; polyalkenes and polyalkene oxides; polyethylene glycol. Clearly there may be other suitable materials, and the above are given merely as examples. One or more fusible materials may be present. Preferred fusible materials generally function as a binder for other components in the powder.

In general the powder material should contain at least 30%, usually at least 35%, advantageously at least 80%, by weight of material that is fusible, and, for example, fusible material may constitute up to 95%, e.g. up to 85%, by weight of the powder. Wax, if present, is usually present in an amount of no more than 6%, especially no more than 3% by weight, and especially in an amount of at least 1% by weight, for example 1 to 6%, especially to 1 to 3%, by weight of the powder material.

Of the materials mentioned above, polymer binders (also referred to as resins) should especially be mentioned. Examples include polyvinylpyrrolidone, hydroxypropyl cellulose, hydroxypropyl methylcellulose phthalate, hydroxypropyl methylcellulose acetate succinate and methacrylate polymers, for example an ammonio-methacrylate copolymer, for example those sold under the name Eudragit.

Often resin will be present with a wax as an optional further fusible component in the core; the presence of a wax may, for example, be useful where fusing is to take place by a contact system for example using a heated roller, or where it is desired to provide a glossy appearance in the fused film. The fusible component may comprise a polymer which is cured during the treatment, for example by irradiation with energy in the gamma, ultra violet or radio frequency bands. For example, the core may comprise thermosetting material which is liquid at room temperature and which is hardened after application to the substrate.

Preferably, the powder material includes a material having a charge-control function. That functionality may be incorporated into a polymer structure, as in the case of Eudragit resin mentioned above, and/or, for a faster rate of charging, may be provided by a separate charge-control additive. Material having a charge-control function may be present in the shell or in the core or in both shell and core. Examples of suitable charge-control agents are as follows: metal salicylates, for example zinc salicylate, magnesium salicylate and calcium salicylate; quaternary ammonium salts; benzalkonium chloride; benzethonium chloride; trimethyl tetradecyl ammonium bromide (cetrimide); and cyclodextrins and their adducts. One or more charge-control agents may be used. Charge-control agent may be present, for example, in an amount of up to 10% by weight, especially at least 1% by weight, for example from 1 to 2% by weight, based on the total weight of the powder material.

The powder material may also include a flow aid. The flow aid reduces the cohesive and/or other forces between the particles of the material to improve the flowability of the powder. Suitable flow aids (which are also known as "surface additives") are, for example, as follows: colloidal silica; metal oxides, e.g. fumed titanium dioxide, zinc oxide or alumina; metal stearates, e.g. zinc, magnesium or calcium stearate; talc; functional and non-functional waxes, and polymer beads, e.g. poly-methyl methacrylate beads, fluoropolymer beads and the like. Such materials may also enhance tribocharging. A mixture of flow aids, for example silica and titanium dioxide, should especially be mentioned. The powder material may contain, for example, 0 to 3% by weight, advantageously at least 0.1%, e.g. 0.2 to 2.5%, of surface additive flow aid.

The powder materials used in the present invention include a colourant and/or an opacifier. When the powder comprises a core and shell such components are preferably present in the core. Examples of suitable colourants and opacifiers are as follows: metal oxides, e.g. titanium dioxide, iron oxides; aluminium lakes, for example, indigo carmine, sunset yellow and tartrazine; approved food dyes; natural pigments. A mixture of such materials may be used if desired. Opacifier preferably constitutes no more than 50%, especially no more than 40%, more especially no more than 30%, for example no more than 10% by weight of the powder material, and may be used, for example, in an amount of at least 5% by weight of the powder. Titanium dioxide is an especially useful opacifier, providing white colour and having good hiding power and tinctorial strength. Colourant present with opacifier may, for example, constitute no more than 10%, preferably from 1 to 5%, by weight of the powder. If there is no opacifier, the colourant may be, for example, 1 to 15%, e.g. 2 to 15%, especially 2 to 10%, by weight of the powder. To achieve optimum colour, amounts of up to 40% by weight of colourant may be needed in some cases, for example if inorganic pigments, e.g. iron oxides, are used. However, the powder material usually contains, for example, from 0 to 25% by weight in total of colourant and/or opacifier.

The powder material may also include a dispersing agent, for example a lecithin. The dispersing agent is preferably present with the colourant/opacifier (that is, preferably in the core), serving to improve the dispersion of the colourant and opacifier, more especially when titanium dioxide is used. The dispersing component is preferably a surfactant which may be anionic, cabonic or non-ionic, but may be another compound which would not usually be referred to as a "surfactant" but has a similar effect The dispersing component may be a co-solvent. The dispersing component may be one or more of, for example, sodium lauryl sulphate, docusate sodium, Tweens (sorbitan fatty acid esters), polyoxamers and cetostearyl alcohol. Preferably, the powder material includes at least 0.5%, e.g. at least 1%, for example from 2% to 5%, by weight of dispersing component, based on the weight of the powder material. Most often it is about 10% by weight of the colourant and opacifier content.

The powder material may also include a plasticiser, if necessary, to provide appropriate rheological properties. A plasticiser may be present in the core and/or the shell, but usually, if present, a plasticiser is included with resin used for the core to provide appropriate rheological properties, for example for preparation of the core by extrusion in a melt extruder. Examples of suitable plasticisers include polyethylene glycols, triethyl citrate, acetyltributyl citrate, acetyltriethyl citrate, tributyl citrate, diethyl phthalate, dibutyl phthalate, dimethyl phthalate, dibutyl sebacate and glyceryl monostearate.

A plasticiser may be used with a resin in an amount, for example, of up to 50% by weight of the total of that resin and plasticiser, the amount depending inter alia on the particular plasticisers used. The powder may contain an amount of up to 50% by weight of plasticiser.

The powder coating material may further include one or more taste modifiers, for example aspartame, acesulfame K, cyclamates, saccharin, sugars and sugar alcohols or flavourings. Preferably there is no more than 5%, more preferably no more than 1%, of flavouring based on the weight of the powder material, but larger or smaller amounts may be appropriate, depending on the particular taste modifier used.

If desired the powder material may further include a filler or diluent. Suitable fillers and diluents are essentially inert and low cost materials with generally little effect on the colour or other properties of the powder. Examples are as follows: alginic acid; bentonite; calcium carbonate; kaolin; talc; magnesium aluminium silicate; and magnesium carbonate.

The particle size of the powder material has an important effect on the behaviour of the material in electrostatic application. Although materials having a small particle size are recognised as having disadvantages such as being more difficult to produce and to handle by virtue of the material's cohesiveness, such material has special benefits for electrostatic application and the benefits may more than counter the disadvantages. For example, the high surface to mass ratio provided by a small particle increase the electrostatic forces on the particle in comparison to the inertial forces. Increasing the force on a particle has the benefit of increasing the force that causes it to move into contact with the substrate, whilst a reduction in the inertia reduces the force needed to accelerate a particle and reduces the likelihood of a particle arriving at the substrate bouncing back off the substrate. However, very small particle sizes may not be achievable where the coating material comprises a high proportion of a particular ingredient, for example a high proportion of active material.

Preferably, at least 50% by volume of the particles of the material have a particle size no more than 100 µm. Advantageously, at least 50% by volume of the particles of the material have a particle size in the range of 5 µm to 40 µm. More advantageously, at least 50% by volume of the particles of the material have a particle size in the range of 5 to 25 µm.

Powder having a narrow range of particle size is especially preferred. Particle size distribution may be quoted, for example, in terms of the Geometric Standard Deviation ("GSD") ratios $d_{90}/d_{50}$ or $d_{50}/d_{10}$ where $d_{90}$ denotes the particle size at which 90% by volume of the particles are below this figure (and 10% are above), $d_{10}$ represents the particle size at which 10% by volume of the particles are below this figure (and 90% are above), and $d_{50}$ represents the mean particle size. Advantageously, the mean ($d_{50}$) is in the range of from 5 to 40 µm, for example, from 5 to 25 µm. Preferably, $d_{90}/d_{50}$ is no more than 1.5, especially no more than 1.35, more especially no more than 1.32, for example in the range of from 1.2 to 1.5, especially 1.25 to 1.35, more especially 1.27 to 1.32, the particle sizes being measured, for example, by Coulter Counter. Thus, for example, the powder may have $d_{50}=10$ µm, $d_{90}=13$ µm, $d_{10}=7$ µm, so that $d_{90}/d_{50}=1.3$ and $d_{50}/d_{10}=1.4$.

While colour separation has been achieved using powder having mean particles sizes of 6 µm and 12 µm it is easier to achieve colour separation with a large difference e.g. using powders having mean particle sizes of 6 µm and 18 µm.

If colour separation is to be achieved using charge differential between the particles it is preferred that the difference is at least 15 µ coulombs per gram, more preferably 25 µ coulombs per gram.

The powder material is fusible so that it is treatable to form a continuous film coating.

It is important that the powder can be fused or treated without degradation of any active material in the powder and without degradation of the tablet core. For some materials it may be possible for the treatment step to involve temperatures up to and above 250° C. Preferably, however, the powder material is fusible at a pressure of less than 100 lb/sq. inch, preferably at atmospheric pressure, at a temperature of less than 200° C., and most commonly below 150° C., and often at least 80° C., for example in the range of from 100 to 140° C.

Fusing of the powder material may be carried out by any of a number of different fusing methods. The powder material is preferably fused by changing the temperature of the powder, for example by radiant fusing using electromagnetic radiation, for example infra red radiation or ultraviolet radiation, or conduction or induction, or by flash fusing. The amount of heat required may be reduced by applying pressure to the powder material, for example by cold pressure fusing or hot roll fusing.

Preferably, the powder material has a glass transition temperature (Tg) in the range of 40° C. to 120° C. Advantageously, the material has a Tg in the range of 50° C. to 100° C. A preferred minimum Tg is 55° C., and a preferred maximum Tg is 70° C. Accordingly, more advantageously, the material has a Tg in the range of 55° C. to 70° C.

Generally, the powder material should be heated to a temperature above its softening point, and then allowed to cool to a temperature below its Tg.

The invention will be illustrated by the following Examples in which all parts and percentages are by weight unless otherwise stated.

In the Examples reference will be made to the accompanying drawings in which.

EXAMPLE 1

A tablet of diameter 10 mm has a convex spherical surfaces on either side with a radius of 10 mm. In one of these surfaces a simple pattern is formed with orthogonal grooves approximately 1 mm square in cross-section. The grooves are cut with parallel sides substantially perpendicular to the upper surface of the tablet, with the total area of the groove bases being no more than 5% of the area of the respective tablet face. The entire surface was then subjected to electrodeposition of a mixture of blue particles carrying a charge of 40 µcoulombs per gram and red particles carrying a charge of 15 µcoulombs per gram. The electrodeposition technique used was that described in our European Patent Publication No: 0 824 344 (WO96/35413) and 0 869 847 (WO96/35516) referred to above. After fusing the particles, the exposed tablet surface appeared as a dull red, with the grooves being clearly identified in blue. The blue at the base of the grooves clearly demonstrated that the blue particles were preferentially attracted to these regions. The dull red at the upper surface indicates that the red particles have predominated in these regions, although not without some influence from the blue.

EXAMPLE 2

Example 1 was repeated, but using yellow particles charged at 25 µcoulombs per gram in place of the red particles. The result was similar in that the basis of the grooves where clearly coloured blue, but the upper surface in this case appeared grey, as a consequence of the more balanced mixture of yellow and blue particles in these regions. The reason for this is the smaller differential between the charge applied to the yellow and blue particles (15 µcoulombs per gram) compared to that between the charge applied to the red and blue particles (25 µcoulombs per gram).

EXAMPLES 3 and 4

The procedures described in Examples 1 and 2 above were repeated using a tablet formed with a multitude of individual recesses, rather than individual grooves. The results were essentially similar, with blue in each case being concentrated at the base of each recess, and the upper surface of the table being uniformly a dull red or grey respectively.

EXAMPLES 5 to 8

Tablet cores were prepared from the following powder formulation:

| | |
|---|---|
| Dibasic calcium phosphate (anhydrous) | 95% |
| sodium starch glycolate | 4% |
| Magnesium stearate | 1% |

Figure 1:
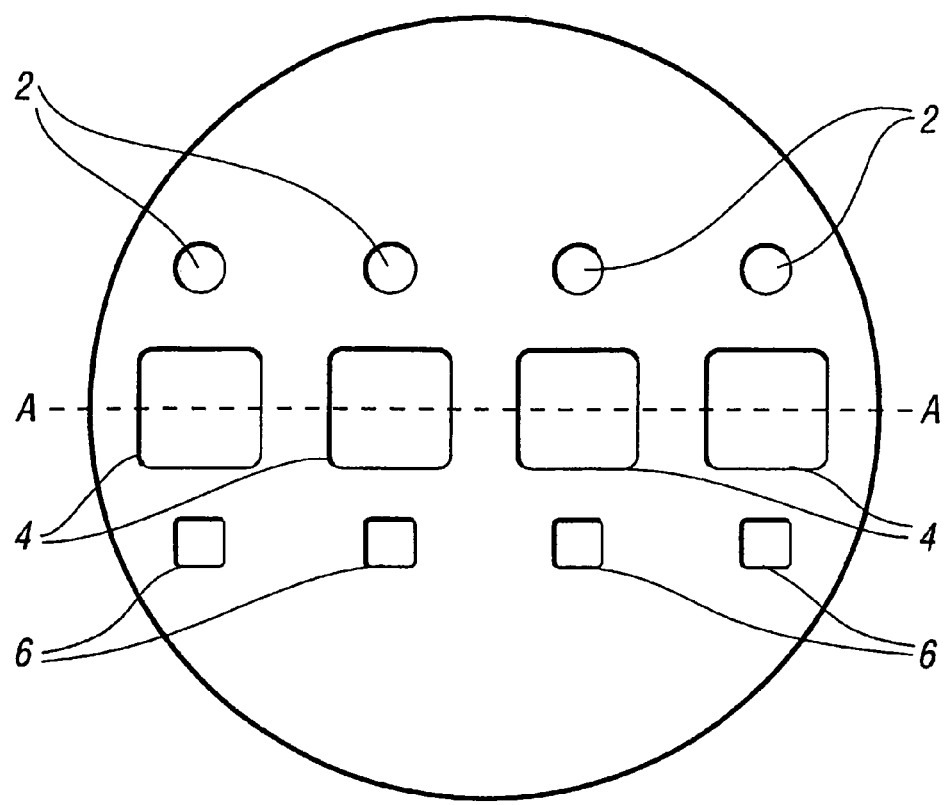
FIG. 1 represents the plan view of a tablet core.
Figure 2:
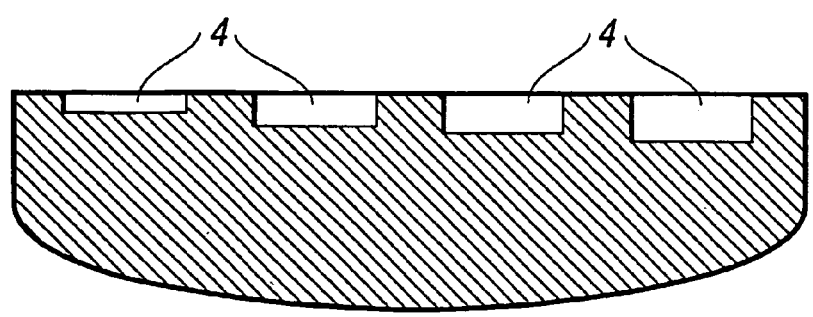
FIG. 2 represents a cross-sectional view along the line AA in FIG. 1.

The powder was compressed using patterned flat punches to form tablets, diameter 10 mm, thickness 4.0 mm, hardness of 10 to 15 kPa. The resulting tablets had indentations of three different shapes with four different depths as illustrated in FIGS. 1 and 2. The shapes were circles (2) with diameters of 0.5 mm and squares (4) with 1.8 mm sides and squares (6) with 0.5 mm sides, the squares having rounded corners (FIG. 1). The indentations had depths of 0.1, 0.2, 0.4 and 0.6 mm as shown in the cross-section in FIG. 2. These tablet cores were used in Examples 5 to 8.

EXAMPLE 5

The following powder formulations were prepared:

| Yellow powder having a mean particle size (D50) of 6 µm | |
|---|---|
| Eudragit E100 | 85% |
| TiO$_2$ | 10% |
| Riboflavin | 5% (yellow colour) |

| Blue powder having a mean particle size (D50) size of 12 µm | |
|---|---|
| Eudragit E100 | 85% |
| TiO$_2$ | 10% |
| Indigo carmine lake | 5% (blue colour) |

Each powder was added at 5% by weight to a strontium ferrite carrier FCX6468 (Kynar) having an average particle size at 27 µm. The resulting powder was applied to the tablet using a proprietary Electrophotographic dual component magnetic brush development system as disclosed in WO01/43727. Coating conditions: Magnet speed 1500 rpm, 1.4 mm sleeve to tablet surface gap. Brush trim adjusted to 0.6 mm to give brush thickness of approximately 1.2 mm.

Figure 3:
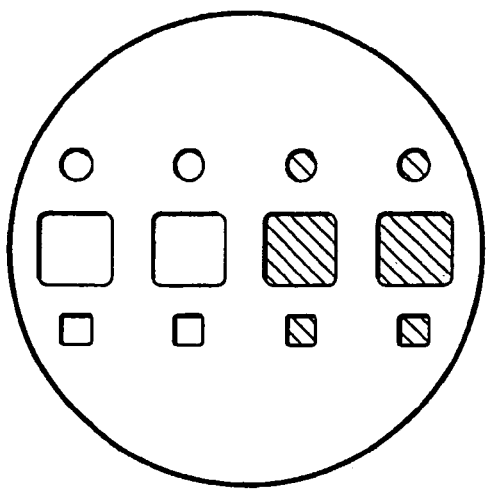
FIGS. 3 to 5 represent plan views of coated tablets showing the colour separation achieved by Examples 5 to 7 respectively.

The tablets were passed over the developer system four times at 25 mm/s. Using a 1 kHz square wave development field of 4000 V, offset by 400 V the two powders were distributed (without the carrier) so that the 0.4 and 0.6 mm deep indentations appeared coloured blue while the other indentations and the face of the tablet appeared green. The vertical walls of the tablet also appeared blue. FIG. 3 represents the colouration of the tablet, the shaded areas representing blue and the unshaded areas representing green. This Example demonstrates that difference in particle size allows colour separation.

EXAMPLE 6

The following powder formulation was prepared:

| Red powder having a mean particle size (D50) of 18 µm | |
|---|---|
| Eudragit E100 | 85% |
| TiO$_2$ | 10% |
| Ponceau 4 R lake | 5% (red colour) |

The red powder and the yellow powder from Example 5 were mixed with the strontium ferrite carrier and applied to the tablet cores under the same condition as Example 5.

Figure 4:
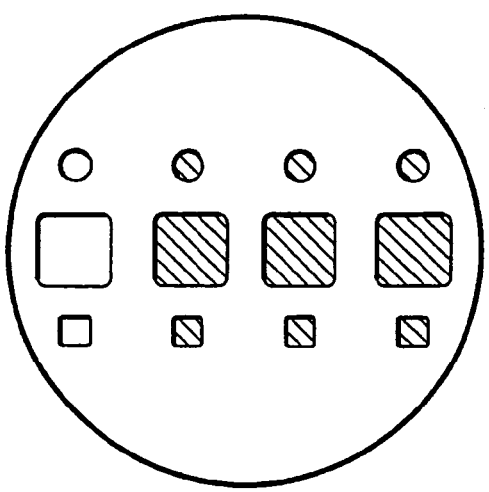

In this case the powders became distributed so that the 0.2, 0.4 and 0.6 mm indentations and sides of the table appeared red while the face of the tablet was yellow. FIG. 4 represents the colouration of the tablet, the shaded areas representing red and the unshaded areas representing yellow.

The Example demonstrates that improved colour separation can be achieved if the particle size different between the powders is large.

EXAMPLE 7

Figure 5:
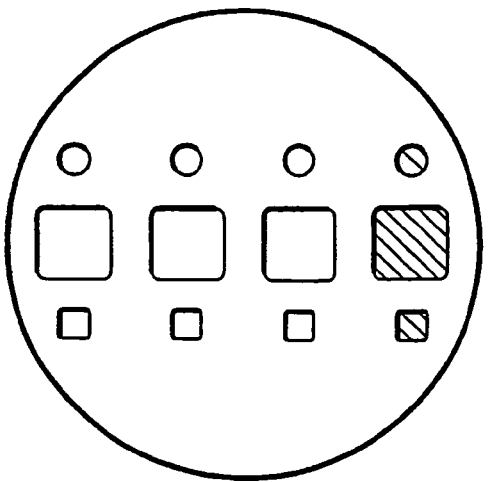

The same powder formulation as Example 6 was applied under similar conditions but with a development field frequency of 1250 Hz. Under these conditions the colour separation was most discernible with the 0.6 mm indentations. FIG. 5 represents the colouration of the tablet, the shaded areas representing red and the unshaded areas representing yellow.

EXAMPLE 8

In this Example two powders with quite different formulae resulting in different charge but the same particle size distributions were mixed. The D50 of each powder was 12 μm. Each component was added as 5% by mass to a strontium ferrite carrier FCX 6367 (Knyar, 48 μm).

| Blue Powder | |
|---|---|
| Eudragit E100 | 85% |
| TiO$_2$ | 10% |
| Indigo carmine lake | 5% (blue colour) |
| Red Powder | |
| PVP-VA S630 | 63.5% |
| PEG 3000 | 4% |
| E100 | 20% |
| TiO$_2$ | 10% |
| Ponceau 4R lake | 2.5% (red colour) |

When applied to the tablet as in Example 5 but using a 1 kHz square wave development field of 3000 V offset by 400 V, it was found that the blue colour predominated in the 0.6 mm deep indentations. The face of the tablet was purple, suggesting a mix of the two powders.

The example demonstrates that colour separation can be achieved with the same particle size distribution with powder of different charge.

The invention claimed is:

1. A tablet comprising a core which is at least partially coated with an outer layer in the form of a continuous film coating obtained by electrostatic deposition of a powder comprising particles of at least two different colours and subsequent fusing of the deposited powder to form the film characterised in that a surface of the tablet coated with said outer layer is contoured to provide higher regions and lower regions, the outer layer having a first colour in said lower regions and a second colour different from the first colour in said higher regions.

2. A tablet according to claim 1 in the form of a pharmaceutical unit dose.

3. A tablet according to claim 2 wherein there is a depth between said higher and lower regions of at least 0.4 mm.

4. A tablet according to claim 2 wherein there is a boundary between said higher and lower regions which is vertical or substantially vertical.

5. A tablet according to claim 2 wherein said contoured surface defines a pattern, letter, numeral, word, logo or any combination thereof.

6. A method of coating a surface of a tablet to create a coloured pattern thereon, which comprises:
    providing a tablet having a surface which is contoured to provide higher regions and lower regions,
    electrostatically depositing a powder comprising particles of at least two different colours to said tablet surface, particles of one colour being charged to a different level and/or having a different particle size to the particles of the other colour, whereby the higher charged particles or particles of larger particle size preferentially deposit as an outer layer on said lower regions and
    fusing the deposited particles to form a layer in the form of a continuous film coating having a first colour in said lower regions and a second colour different from the first colour in said higher regions.

7. A method according to claim 6 wherein said tablet is in the form of a pharmaceutical unit dose.

8. A method according to claim 7 wherein there is a depth between said higher and lower regions of at least 0.4 mm.

9. A method according to claim 7 wherein there is a boundary between said higher and lower regions which is vertical or substantially vertical.

10. A method according to claim 7 wherein said contoured surface defines a pattern, letter, numeral, word, logo or any combination thereof.

11. A method according to claim 7 wherein the mean particle size of the particles of one colour differs from the mean particle size of the particles of the other colour by at least 6 μm.

12. A method according to claim 11 wherein the mean particle size of the particles of one colour differs from the mean particle size of the particles of the other colour by at least 12 μm.

13. A process according to claim 7 wherein the charge differential between the particles of one colour and those of the other colour is at least 15 μcoulombs per gram.

14. A method according to claim 13 wherein the charge differential between the particles of one colour and those of the other colour is at least 25 μcoulombs per gram.

15. A method according to claim 7 wherein the development field during electrostatic deposition has an AC component.

16. A method according to claim 15 wherein said development field is in the range 1 to 7 kV and has a frequency in the range 500 to 4000 Hz.

17. The method of claim 6 wherein quantities of the two differently coloured particles are mixed each with the other and simultaneously applied to said tablet surface.

18. A tablet comprising a core and an outer layer in the form of a continuous film coating at least partially coating the core, wherein the core is contoured to provide lower and higher regions, and the outer layer is obtained by electrostatic deposition of a powder comprising particles of at least two different colours having different charges and/or different particle sizes, and the coloured particles bearing a higher charge and/or larger particle size are preferentially deposited in the lower regions of the outer layer such that the outer layer has a first colour in said lower regions and a second colour different from the first colour in said higher regions.

* * * * *